(12) United States Patent
Sunavala-Dossabhoy et al.

(10) Patent No.: US 10,363,117 B2
(45) Date of Patent: Jul. 30, 2019

(54) OVERLOAD FAILURE REDUCING DENTAL IMPLANTS

(71) Applicants: Gulshan Neville Sunavala-Dossabhoy, Shreveport, LA (US); Kevin McCarthy, Shreveport, LA (US)

(72) Inventors: Gulshan Neville Sunavala-Dossabhoy, Shreveport, LA (US); Kevin McCarthy, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 3 days.

(21) Appl. No.: 15/151,814

(22) Filed: May 11, 2016

(65) Prior Publication Data

US 2017/0325916 A1    Nov. 16, 2017

(51) Int. Cl.
*A61C 8/00* (2006.01)

(52) U.S. Cl.
CPC .......... *A61C 8/0086* (2013.01); *A61C 8/0013* (2013.01); *A61C 8/0066* (2013.01); *A61C 8/0089* (2013.01); *A61C 8/0022* (2013.01)

(58) Field of Classification Search
CPC ... A61C 8/0056; A61C 8/0057; A61C 8/0059; A61C 8/0062; A61C 8/0065; A61C 8/0033
USPC ........................................................ 433/169
See application file for complete search history.

(56) References Cited

U.S. PATENT DOCUMENTS

| | | | | |
|---|---|---|---|---|
| 3,827,145 A * | 8/1974 | Richards | .............. | A61C 8/0036 433/175 |
| 3,955,280 A * | 5/1976 | Sneer | ................... | A61C 8/0009 433/169 |
| 4,270,905 A * | 6/1981 | Mohammed | ........... | A61C 8/005 433/173 |
| 5,026,280 A * | 6/1991 | Durr | .................... | A61C 8/0086 433/173 |
| 5,049,073 A * | 9/1991 | Lauks | .................. | A61C 8/0018 433/169 |
| 5,213,500 A * | 5/1993 | Salazar | ................ | A61C 8/0018 433/169 |
| 5,362,234 A * | 11/1994 | Salazar | ................ | A61C 8/0024 433/169 |
| 5,437,551 A * | 8/1995 | Chalifoux | ............ | A61C 8/0018 433/172 |
| 5,766,009 A * | 6/1998 | Jeffcoat | ................ | A61C 8/0033 433/173 |
| 6,193,516 B1 * | 2/2001 | Story | ................... | A61C 8/0086 433/173 |
| 7,682,152 B2 * | 3/2010 | Ford | .................... | A61C 8/0086 433/169 |
| 2005/0112397 A1 * | 5/2005 | Rolfe | ................. | A61B 17/8605 428/593 |

(Continued)

*Primary Examiner* — Wade Miles
*Assistant Examiner* — Drew S Folgmann
(74) *Attorney, Agent, or Firm* — Davis & Bujold PLLC; Michael J. Bujold

(57) ABSTRACT

A dental implant including a base, a central shaft and a shock absorber spacing and allowing limited movement between the base and the central shaft. The shock absorber may also contain a plurality of flex struts. The dental implant may further include an index collar covering an upper portion in the base.

20 Claims, 9 Drawing Sheets

(56) References Cited

U.S. PATENT DOCUMENTS

| | | | |
|---|---|---|---|
| 2010/0086896 A1* | 4/2010 | Gieselmann | A61C 8/0012 433/173 |
| 2012/0202173 A1* | 8/2012 | Seo | A61C 8/0025 433/220 |
| 2013/0011814 A1* | 1/2013 | Battula | A61C 8/0006 433/174 |
| 2013/0288200 A1* | 10/2013 | Battula | A61C 8/008 433/173 |
| 2015/0140508 A1* | 5/2015 | Nike | A61C 8/0065 433/172 |
| 2015/0147721 A1* | 5/2015 | Costa Codina | A61C 8/005 433/174 |

* cited by examiner

OVERLOAD FAILURE REDUCING DENTAL IMPLANTS

BACKGROUND OF THE INVENTION

Dental implants have become a standard treatment option for replacement of lost teeth. Osseointegration of implants are important to their success. However, despite many years of use, periodontal infection and heavy occlusal forces that disrupt osseointegration remain major risk factors for implant failure. Occlusal forces on osseointegrated oral implants according to currently practiced technology can cause bone loss and implant failures. The concentration of occlusal forces on peri-implant bone especially, in context of periodontal inflammation, negatively affects implant success. For the foregoing reasons, there is a pressing, but seemingly irresolvable need for improved oral implants.

SUMMARY OF THE INVENTION

Wherefore, it is an object of the present invention to overcome the above mentioned shortcomings and drawbacks associated with the current technology. The present invention is directed to methods and devices that satisfy the above shortcomings and drawbacks. The method and apparatus comprise an oral implant having a base, a central shaft, and a shock absorber.

According to further embodiments, the dental implants may include an index collar covering an upper portion in the base. A first end of at least one of the plurality of flex struts may be attached to a strut portion of the central shaft and a second end of the at least one of the plurality of flex struts may be attached to one of an inner surface of the base and an inner surface of the index collar. The plurality of flex struts may attach to the strut portion of the central shaft at a plurality of circumferential locations along the central shaft and a plurality of axial locations along the shaft. The central shaft may pass through an index aperture, where the index aperture is defined in the index collar. The index aperture may be located in a substantially radially central location on the index collar. The central shaft may have index tabs arranged along a circumference of the central shaft. The index tabs may be shaped to mate with the index aperture. The index collar may form an upper membrane on the base. A lowest portion of the strut portion of the central shaft may be proximate to but spaced from an inner surface of the base. The central shaft may resiliently move between 0.1 mm and 1.0 mm with respect to the base when a force of between 70 to 150 Newtons is applied to the central shaft. The index collar may be made of one of titanium metal and a titanium alloy. The central shaft may include an attachment portion fitted to attach to a tooth attachment. A tooth attachment may be attached to an attachment portion of the central shaft. The base may have an outer surface that includes a porous metal. The porous metal may be one of titanium, tantalum, and an alloy including one titanium, tantalum, and both titanium, tantalum. The porous metal may be one of foam and coated with calcium phosphate, hydroxyapatite, derivatives of each or combinations including one or more thereof. The second end of a first plurality of flex struts may be attached the inner surface of the base and the second end of a second plurality of flex struts is attached to the inner surface of the index collar. A Z axis may be defined by the central shaft, wherein the central shaft is rotationally fixed about the Z axis with respect to the index collar and the base, and index collar at the collar aperture acts as a fulcrum for the central shaft allowing the central shaft to resiliently increase obliquity about the collar aperture.

Various objects, features, aspects, and advantages of the present invention will become more apparent from the following detailed description of preferred embodiments of the invention, along with the accompanying drawings in which like numerals represent like components.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which.

DETAILED DESCRIPTION OF THE PREFERRED EMBODIMENTS

Figure 1:
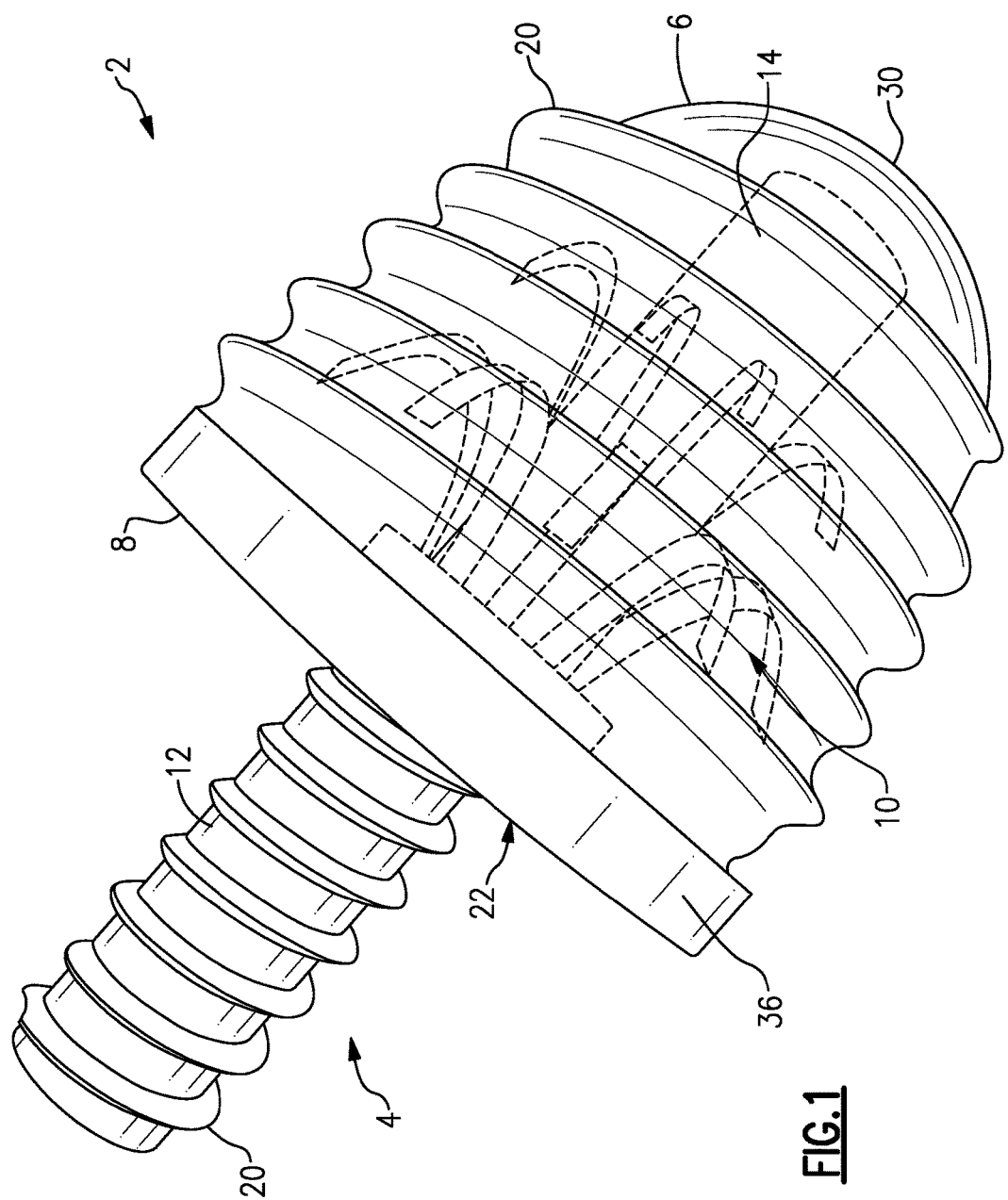
FIG. 1 is a side perspective view of a first embodiment of a dental implant according to the present invention with the base partially ghosted or see through to show the strut portion of the central shaft and the flex struts.
Figure 2:
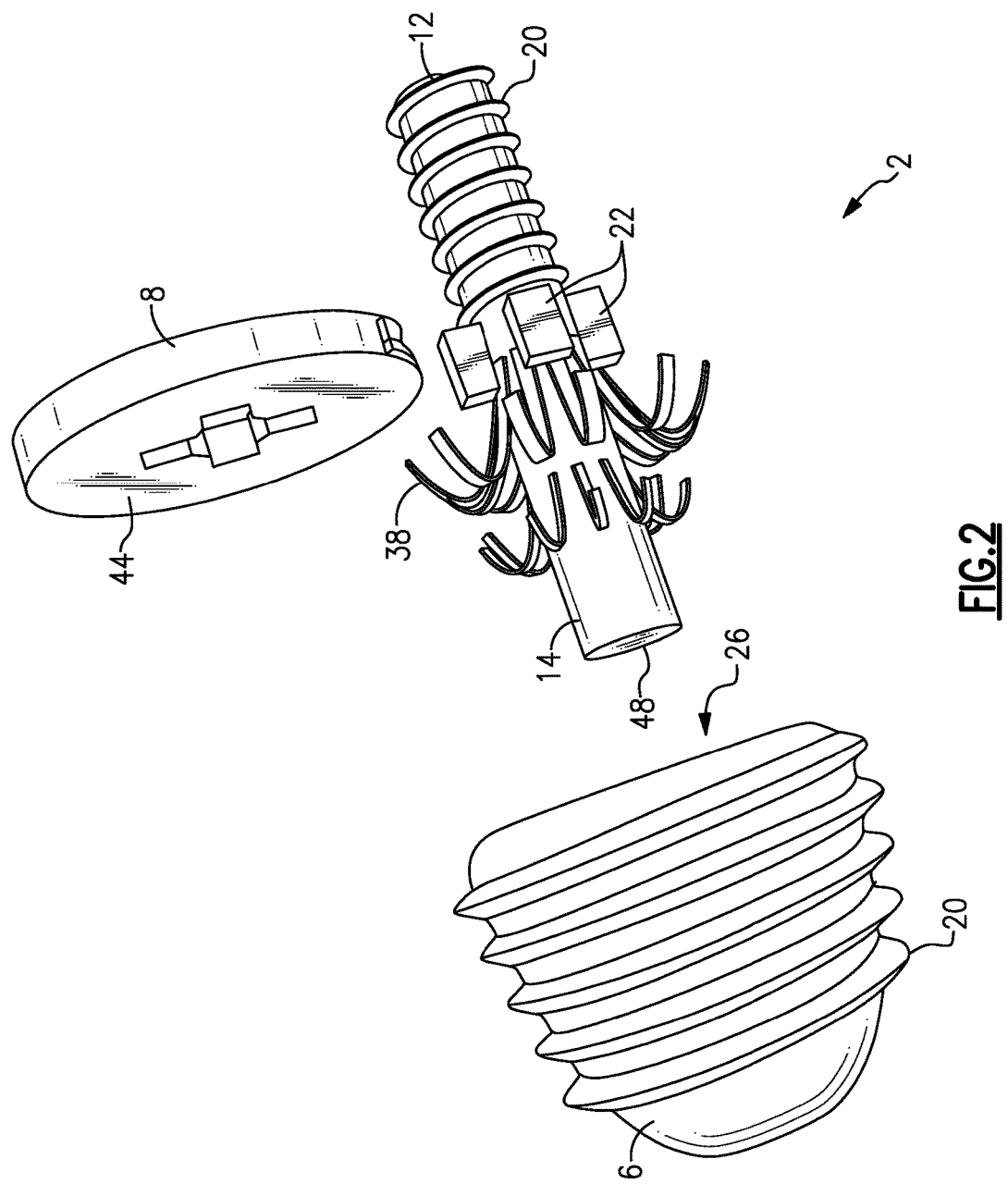
FIG. 2 is an exploded perspective view of the dental implant of FIG. 1.

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

The jaw bone is subject to mechanical loading, and it remodels in response to the stresses and strains of the oral environment. The bone's response to increasing magnitudes of mechanical strain is (a) disuse atrophy (approximately 50-100µε), (b) steady state (approximately 100-1500µε) (c) mild overload (approximately 1500-300µε), and (d) fatigue failure (approximately >3000µε). Mild strain conditions can increase reactive woven bone formation, but the newly formed bone is less mineralized and weaker. Whereas greater stresses cause microfractures, fibrous tissue formation, and bone resorption.

Excessive loads disrupt implant osseointegration and increase implant micromotion with respect to the bone. Marginal bone loss beside the implant is a complication with implants according to currently practiced technology. Animal studies have demonstrated the role of implant overload in bone loss and implant failure. The inventors observed that an implant design that dissipates compressive and shear forces is greatly preferable to reducing stresses on interface bone and maintaining the bone's structural integrity.

Mastication involves the loading of teeth in a repetitive manner. The periodontal ligament, sandwiched between the tooth and the bone, is composed of collagen fibers that act as shock absorbers to dissipate the load and reduce stress concentration. Implants mostly used in current clinical practice are solid screws that provide no cushioning of forces levied on them. To decrease the compressive forces on the bone abutting the implant, the inventors have invented an oral implant that better mimics the function of the periodontal ligament in a three-dimensional response to stress.

Turning now to FIG. 1, a brief description concerning the various components of the present invention will now be briefly discussed. As can be seen in this embodiment, the dental implant 2 comprises a central shaft 4, a base 6, an index collar 8, and a shock absorber 10.

Central Shaft:

The central shaft 4 has a first preferably threaded attachment portion 12 and a second preferably smooth strut portion 14. The attachment portion 12 allows a tooth attachment 16 having a mating threaded hole 18 to be screwed onto the central shaft 4. The tooth attachment 16 is preferably a dental prostheses including a crown, bridge, denture, and facial prosthesis.

The threads 20 may be omitted on the attachment portion 12 if another method is used to secure the tooth attachment 16 to the central shaft 4. The central shaft 4 extends through the index collar 8 with the strut portion 14 extending into the base 6. Preferably, a plurality of index tabs 22 are provided along a circumference of the central shaft 4, adjacent to the index collar 8. The index tabs 22 provide an engagement location for a tightening tool to rotate the index tabs 22, and thus also rotating the index collar 8 and the base 6, thereby securing the base 6 and thus the remainder of the dental implant 2 into the bone 24 of the patient.

The attachment portion 12 and the strut portion 14 of the central shaft 4 may be formed of a single unit of unitary construction, as shown. Alternatively, the attachment portion 12 may be initially separate from the strut portion 14 such that the strut portion 14 and the base 6 may be inserted into the bone 24 and allowed to bond with the bone 24 without first attaching the attachment portion 12. At a later time, for example, the attachment portion 12 and the tooth attachment 16 could be attached to the strut portion 14 through a screw and mating threaded hole, and/or other attachment options, including other mechanical attachments, chemical adhesives including cementing, and physical methods including soldering. Additionally, multiple central shafts, including with one or more offset from a central area of the base 6 may be utilized for greater security in attachment and more even dissipation of strain on the dental implant 2.

Base:

The base 6 will preferably provide a fluid tight envelope between the interior 26 of the base 6 and the exterior environment 28 exterior to the base 6. The base can be seen as an outer shell or hull of a lower portion of the dental implant 2. The outer surface 30 of the base 6 is preferably a metal, such as titanium or tantalum, or non-metal, such as ceramic. The metal would preferably have or be covered with a trabecular or porous structure. The metal may be substantially pure or as an alloy. The metal may be as a foam and/or coated with calcium phosphate, hydroxyapatite, derivatives of each or combinations including one or more thereof to encourage the formation of vascular systems within the porous area and integration into the bone 24. The inner surface 32 of the base 6 defines a void into which the strut portion 14 of the central shaft 4 extends. A terminal end 48 of the strut portion 14 of the central shaft 4 is spaced from the inner surface 32 of the base 6. The interior 26 of the base 6 could be a vacuum, or filled with air, an inert gas, or a gel, for example. The inner surface 32 of the base 6 could be lined with an antimicrobial substance to prevent microbial growth.

Index Collar:

The index collar 8 provides an upper membrane to the interior 26 of the base 6. The index collar 8 is preferably resiliently flexible and water tight—such a titanium sheet metal. The central shaft 4 passes through a collar aperture 34 in the approximate center of the index collar 8. The collar aperture 34 being a through aperture passing through the index collar 8. The index collar 8 is preferably rotationally fixedly secured and sealed to the base 6 along the circumference 36 of the index collar 8. According to a preferred embodiment, the index collar 8 along with the central shaft 4, the flex struts 38, and the base 6 will be cast as a fluid tight single unit 2. According to a further embodiment, a silicon seal may seal the central shaft 4 to the collar aperture 34.

Shock Absorber:

The central shaft 4 is resiliently but flexibly supported via one or more shock absorbers 10 to allow limited movement with respect to the base 6. In the embodiment shown, the central shaft 4 is supported by a plurality of flex struts 38. The flex struts 38 are attached on a first end 40 to the strut portion 14 of the central shaft 4 and on a second end 42 to one of the inner surface 32 of the base 6 and an inner surface 44 of the index collar 8, or both. The flex struts 38 are preferably attached in numerous locations around the circumference of the strut portion 14 and along the axial length of the strut portion 14 to provide uniform force dissipation. The flex struts 38 may be of all the same resiliency, thickness, flexibility, and resistance, or there may be some variation among any or some combination of those qualities among multiple flex struts 38, to provide for some controlled initial movement with a lower amount of force, and additional controlled movement with increased force, or to allow for more movement in a first direction than in a second direction, or to provide for uniform movement in multiple directions with a uniform number of flex struts 38. Though in the embodiment shown the flex struts 38 stop approximately mid-way down the length of the strut portion 14, it is envisioned that the flex struts 38 may continue substantially completely down the length of the strut portion 14 of the central shaft 4. The flex struts 38 will preferably be of sufficient strength that they will prevent the central shaft 4 from touching the inner surface 32 of the base 6 under normal to extreme masticatory forces. The flex struts 38 are preferably metal formed of titanium and/or titanium alloy, and/or a resiliently flexible non-metal materials, including polymers and carbon nano-fibers. The flex struts 38 may be of unitary construction with the central shaft 4 and/or the base 6.

Figure 3:
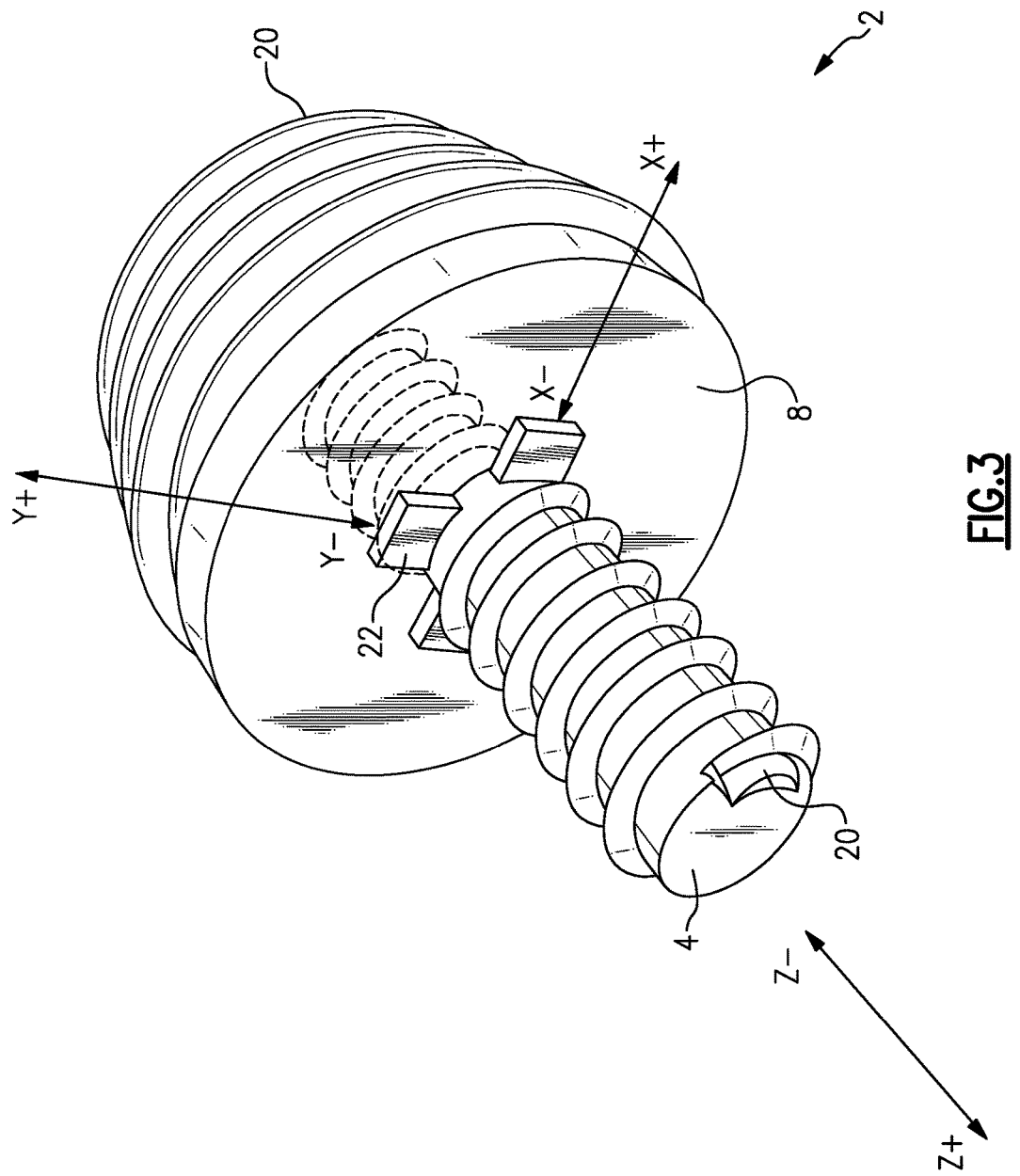
FIG. 3 is a top angled perspective view of the dental implant of FIG. 1.
Figure 4:
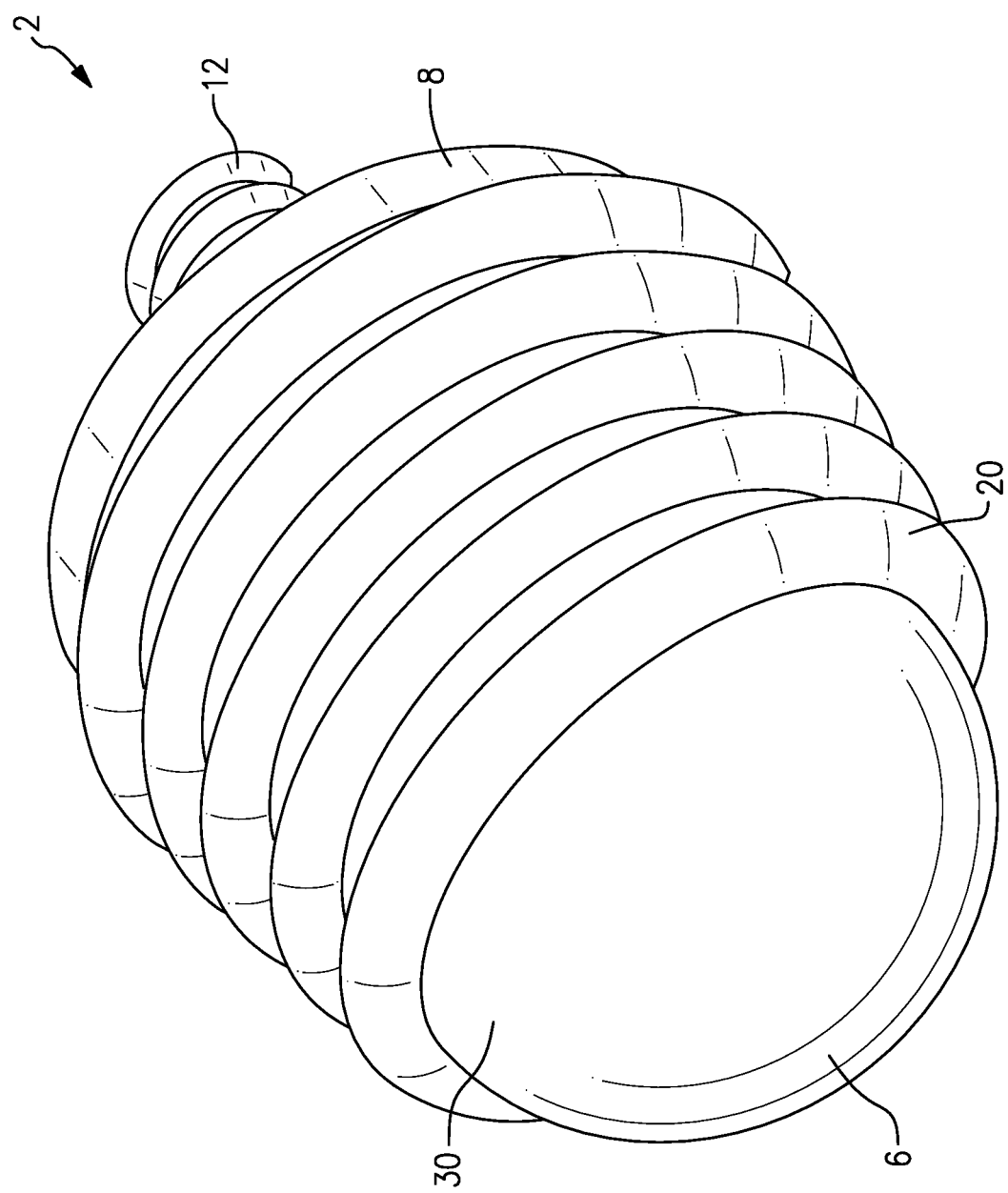
FIG. 4 is a bottom angled perspective view of the dental implant of FIG. 1.
Figure 5:
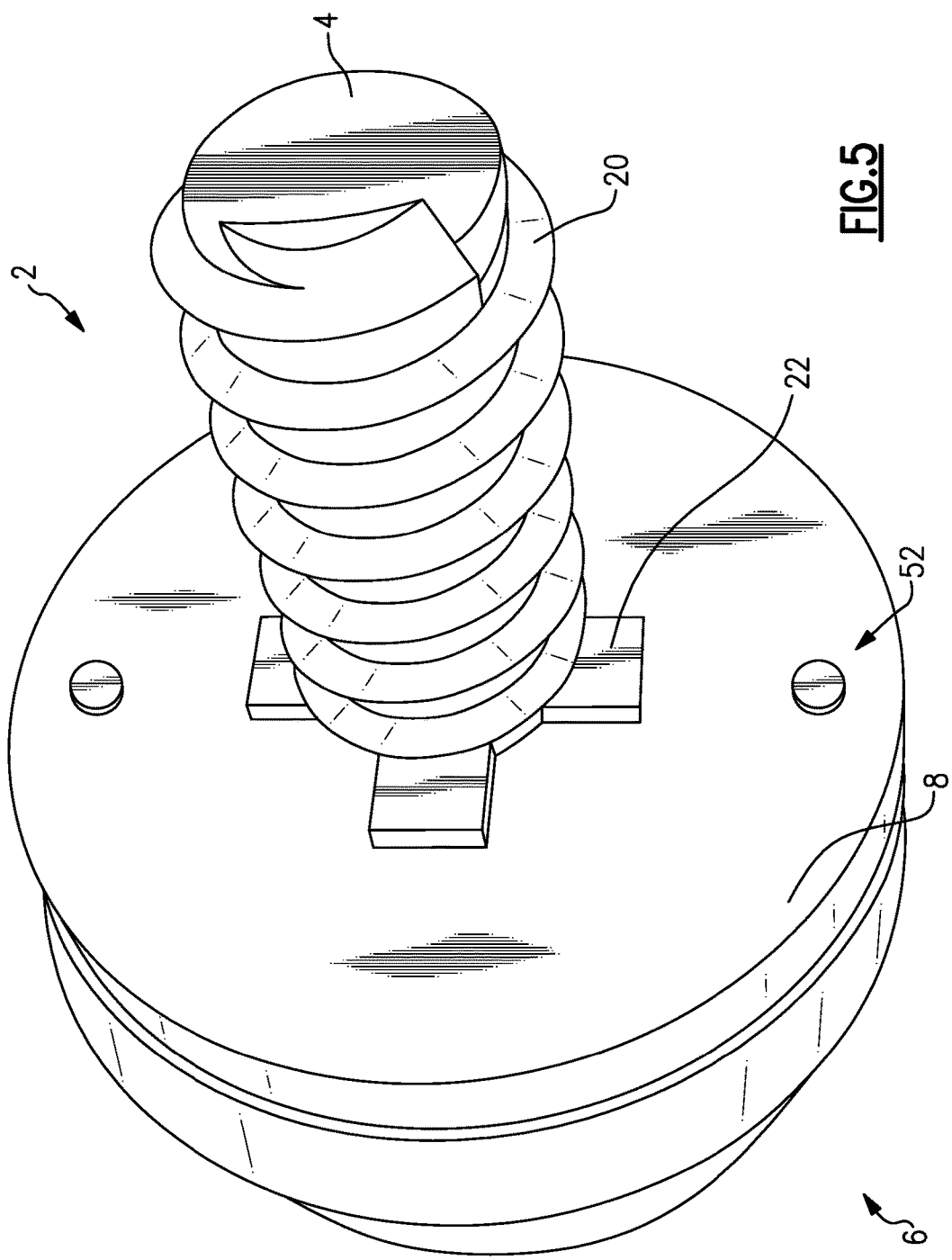
FIG. 5 is a second top angled view of the dental implant of FIG. 1.

The flex struts 38 allow for the central shaft 4, and thus the tooth attachment 16 to move in three dimensions to take pressure off of the bone 24, in the X, Y, and Z directions, where, as shown in FIG. 3, the +, −Z directions are the axial direction defined by the central shaft 4, and the +, −X and +, −Y directions are two axis that are perpendicular to one another and that are also perpendicular to the Z axis. The three dimensional shock absorption spreads the impact force over an increased length of time and more evenly dissipates the force over a larger area of the base 6 and thus the bone 24, decreasing microfractures, fibrous tissue formation, and bone 24 resorption and failure of the implant 2.

The flex struts 38 and the remainder of the implant 2 could be 3D printed, which would convey many benefits, including easy personation of the implant 2 for the mouth and jaw strength of the patient.

It is anticipated that the maximum flexing or movement of the central shaft 4 with respect to the base 6 will be preferably less than 1.0 mm under normal mastication loads—between 70 and 150 Newtons per tooth.

While preferably the multiple flex struts 38 shown help prevent metal fatigue over the life of the implant 2, alternative embodiments include a micro-chip enabled strain gauge on or adjacent to the network of flex struts 38. The micro-chip would preferably be connectable via wireless technology to alert or give a status as to the health or potential failure of the flex struts 38 and even the implant 2 itself if separation from the bone 24 begins to occur.

It is anticipated that the index collar 8 may act as a shock absorber 10 as well, flexing inwards toward the interior 26 of the base 6 and outward away from the interior 26 of the base 6 in response to force placed on the tooth attachment 16.

It is anticipated that the central shaft 4 may pivot, in a rotationally fixed manner, around the collar aperture 34 in the index collar 8, allowing for more controlled movement and more even dissipation of force from the tooth attachment 16 to the central shaft 4 through the shock absorber 10 to the base 6 and then the bone 24.

Alternative embodiments of the shock absorber 10 that may be used instead of or in addition to the flex struts 38 or one another include a hydraulic shock absorber 10. The hydraulic shock absorber embodiment would preferably be between the lower central portion 46 of the inner surface 32 of the base 6 and the lowest portion 48 of the strut portion 14 of the central shaft 4 to provide one dimension of controlled movement. Additional hydraulic shock absorbers 10 may be used in between the side of the inner surface 32 of the base 6 and the side of the strut portion 14 of the shaft to give additional dimensions of movement.

A further additional embodiment of the shock absorber 10 would use coiled springs. The springs would be preferably attached to the circumference of the strut portion 14 of the central shaft 4 and the inner surface 32 of the base 6. Preferably the springs would be attached at least three or more circumferential locations around the strut portion 14 of the central shaft 32. Preferably, an additional one or more coiled springs would be placed between the lower central portion 46 of the interior 26 of the base 6 and the lowest portion 48 of the strut portion 14 of the central shaft 4 to provide resilient shock absorption in the most direct line of mandibular force—along the Z direction.

Figure 6:
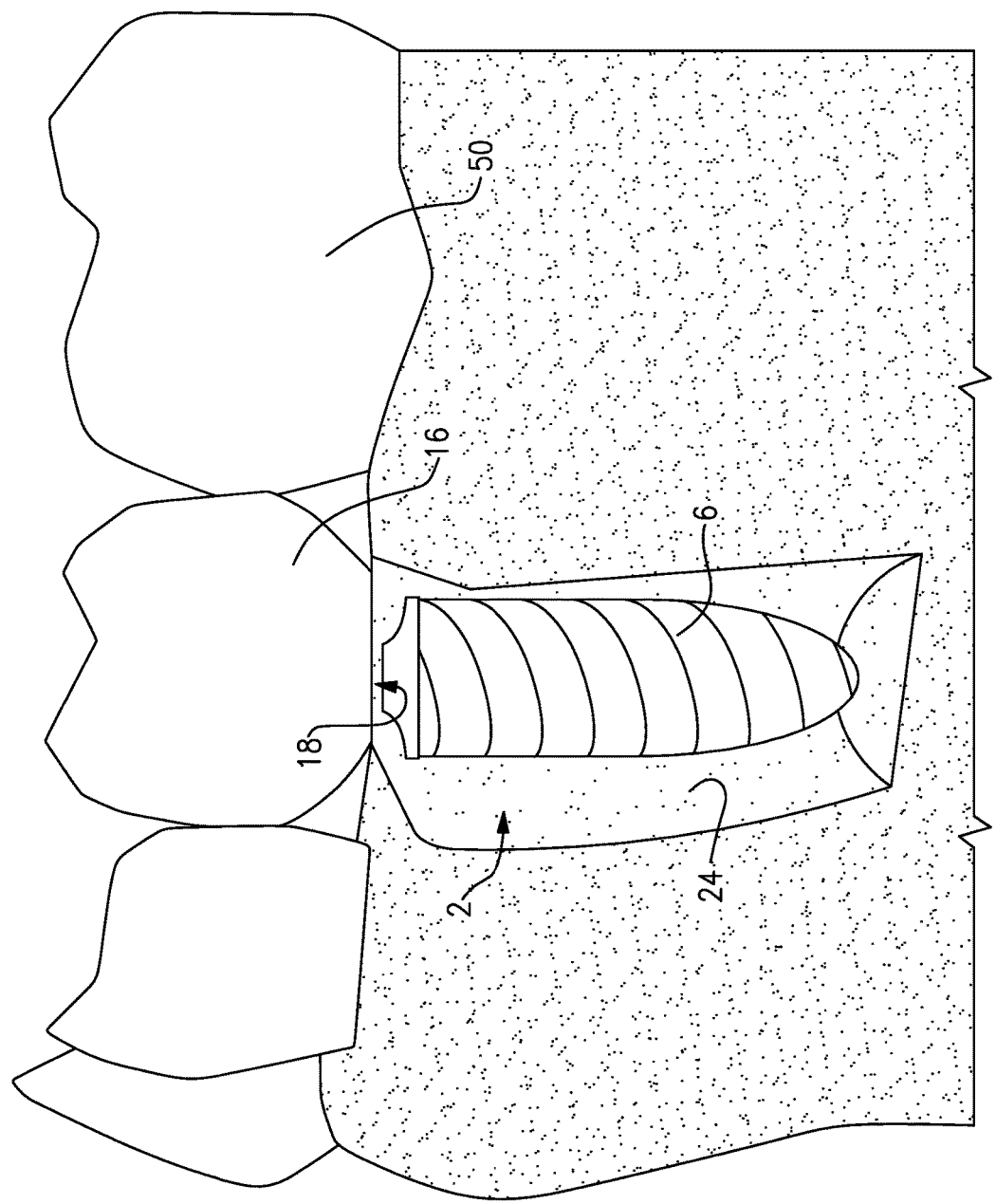
FIG. 6 is a cross sectional view of the dental implant of FIG. 1 implanted into a patient.
Figure 7:
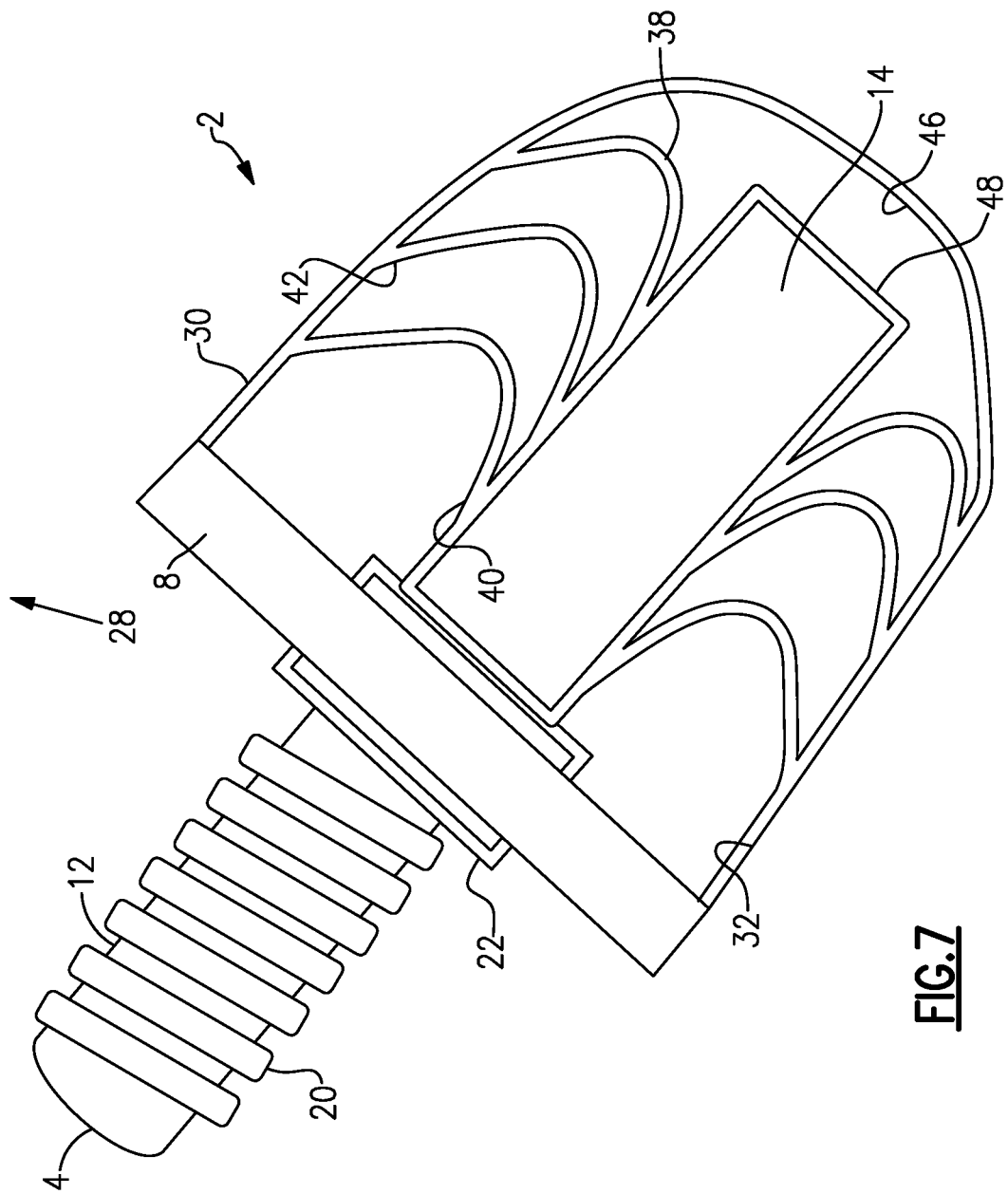
FIG. 7 is a schematic side view of the dental implant of FIG. 1 with the base being see through to show the flex struts and the base threads not shown.
Figure 8:
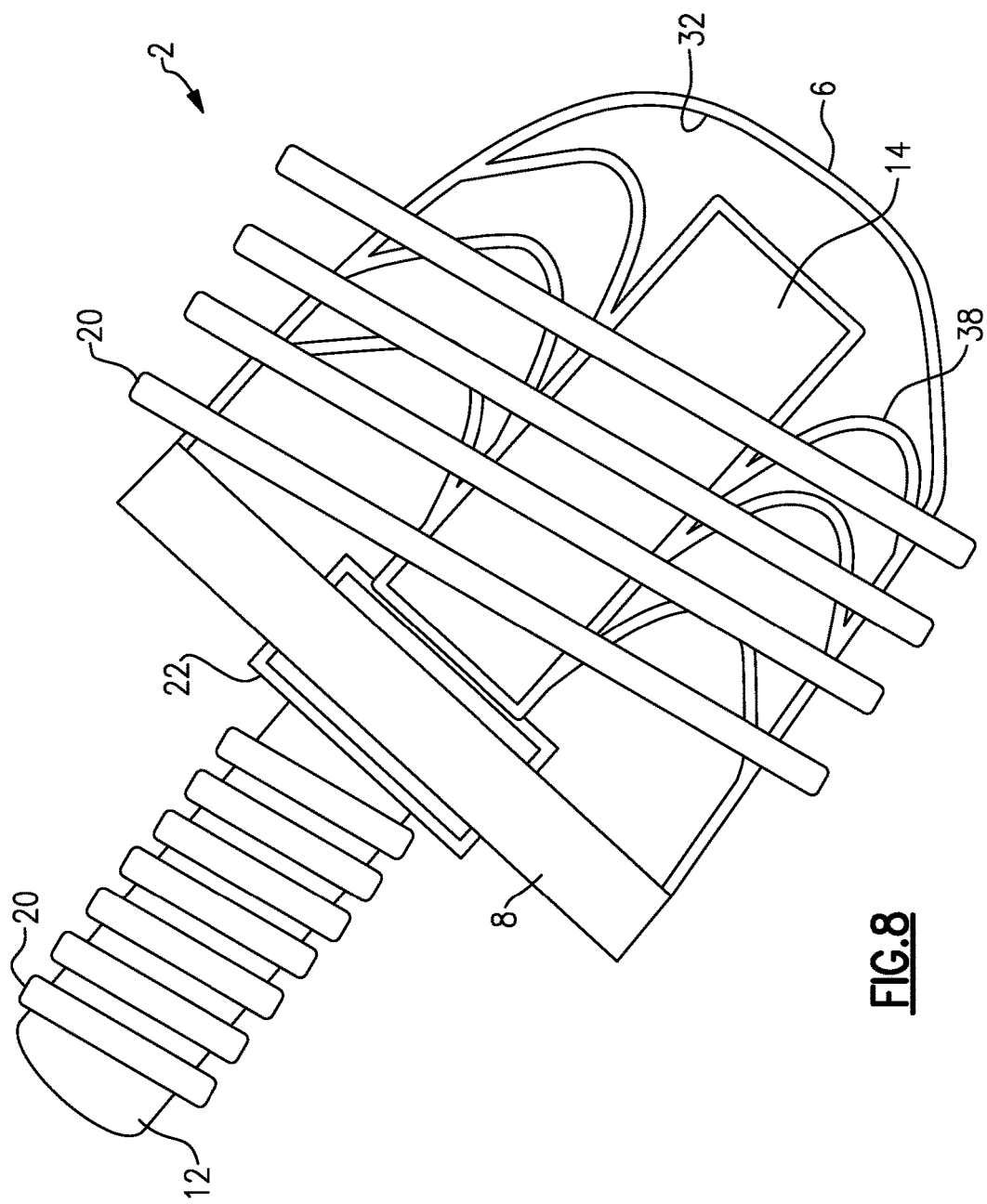
FIG. 8 is a schematic side view of the dental implant of FIG. 7 with the base threads shown.
Figure 9:
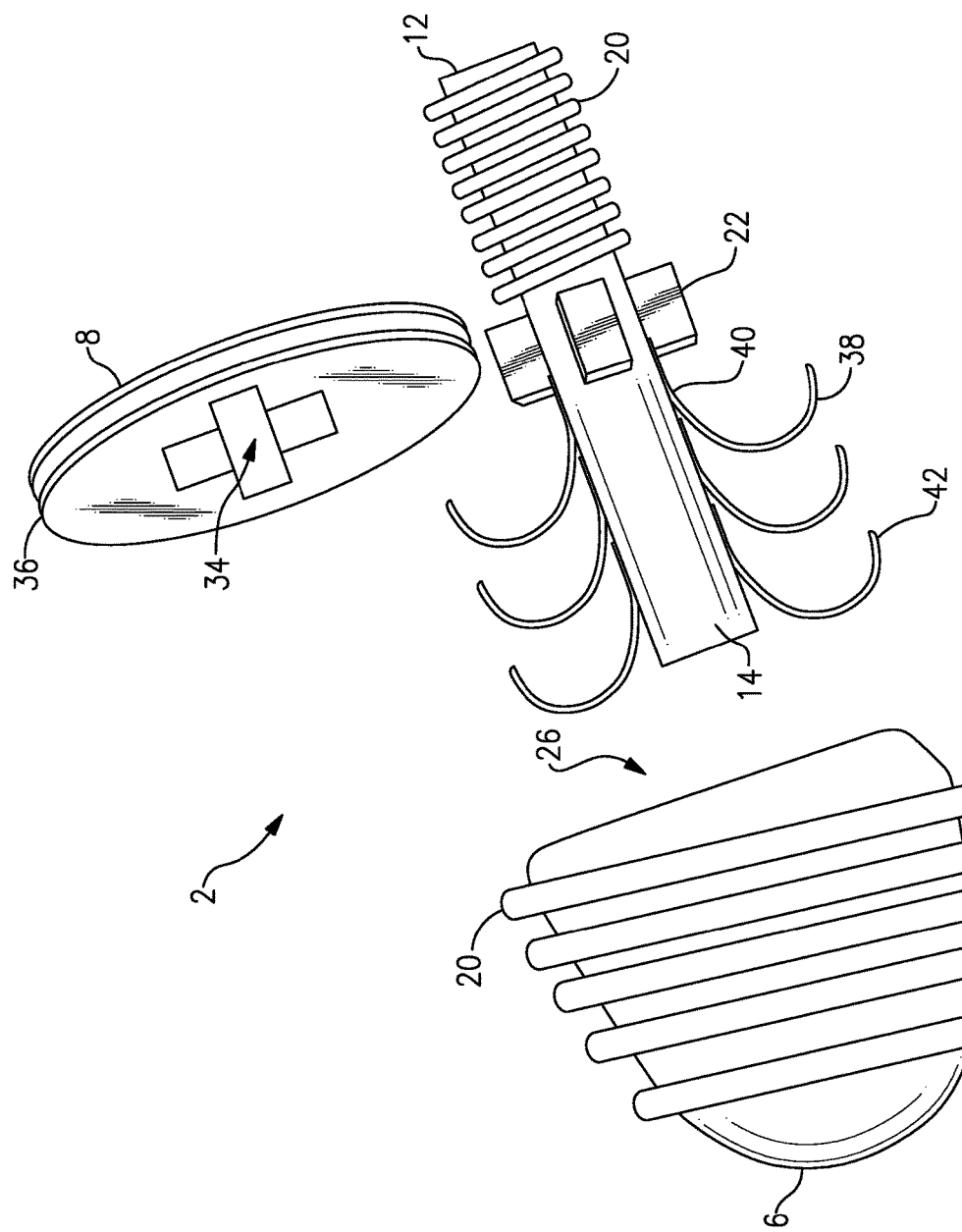
FIG. 9 is a schematic exploded view of the dental implant of FIG. 8.

Inserting:

The dental implant 2 may be inserted into the bone 24 in a similar manner as, for example, screw based implants. The base 6 inserted in the bone 24 is shown in FIG. 6. The tooth attachment 16 adjacent to the patient's teeth 50, providing long term mechanical support for the patient's mastication. Additionally mounting holes or indentations 52 may be provided in the index collar 8 to permit the docking of a spanner-type wrench to the dental implant 2 to facilitate installation into the bone 24 of the patient. The indentations 52 may be through holes fully through the index collar 8 that are sealed after instillation or may be just recesses in the surface of the index collar 8 that maintain the fluid tightness of the membrane created by the index collar 8.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent to those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

We claim:

1. A dental implant comprising:
   a base;
   a central shaft having an external tooth attachment portion adjacent a first end thereof, for engagement with a dental prostheses, and a strut portion, located adjacent a second end of the central shaft, supporting a shock absorber;
   the shock absorber coupling the second end of the central shaft to the base and allowing limited movement between and spacing the base and the central shaft;
   the shock absorber including a plurality of arcuate flex struts;
   wherein a first end of each of the plurality of flex struts are directly attached to the central shaft and a second end of each of the plurality of flex struts are directly attached to the base; and
   each one of the arcuate flex struts initially projects toward the second end of the central shaft before bending back toward the first end of the central shaft and then directly attaching to the base.

2. The dental implant of claim 1 wherein
   the plurality of flex struts have a width, a height, and an elongate length,
   the length extends from the central shaft and connects to the base,
   the length is multiple times the width,
   the length is multiple times the height, and
   the length forms a substantially parabolic shape.

3. The dental implant of claim 2 further comprising an index collar forming an upper membrane of the base, and the index collar interconnects the base to the central shaft.

4. The dental implant of claim 3, wherein the central shaft passes through a collar aperture of the index collar.

5. The dental implant of claim 4, wherein the central shaft has index tabs arranged along a circumference of the central shaft to facilitate rotation and installation of the base of the dental implant into the bone of the patient.

6. The dental implant of claim 5, wherein the index tabs are shaped to mate with the collar aperture.

7. The dental implant of claim 3, further comprising a Z axis defined by the central shaft, wherein the central shaft is rotationally fixed about the Z axis with respect to the index collar and the base, and index collar at the collar aperture acts as a fulcrum for the central shaft allowing the central shaft to resiliently increase an angle of tilt about the collar aperture.

8. The dental implant of claim 4, wherein the index collar is made of one of a pure titanium metal and a titanium metal alloy.

9. The dental implant of claim 1, wherein the plurality of arcuate flex struts are attached to the central shaft at a plurality of circumferential locations along the central shaft and a plurality of axial locations along the central shaft.

10. The dental implant of claim 9, wherein a lowest portion of the strut portion of the central shaft is located proximate to but spaced from an inner surface of the base.

11. The dental implant of claim 9, wherein each of the arcuate flex struts are constructed to permit the central shaft to move resiliently between 0.1 mm and 1.0 mm with respect to the base when a force of between 70 to 150 Newtons is applied to the central shaft.

12. The dental implant of claim 9, further comprising an index collar,
   wherein the second end of at least one second plurality of arcuate flex struts is attached to an inner surface of the index collar,
   the arcuate flex struts are of unitary construction with the base,
   and a majority of a space between the central shaft and the base is filled with of one of a gel, air, and an inert gas or is evacuated.

13. The dental implant of claim 1, wherein the base has an outer surface that is a porous metal.

14. The dental implant of claim 13, wherein the porous metal is one of titanium, tantalum, and alloys thereof.

15. The dental implant of claim 14, wherein the porous metal is one of a foam or coated with one of calcium phosphate, hydroxyapatite, derivatives of calcium phosphate, or derivatives of hydroxyapatite.

16. The dental implant of claim 1 wherein the external tooth attachment portion comprises an external thread for engagement with the dental prostheses.

17. The dental implant of claim 1, wherein at least one index tab is provided along a circumference of the central shaft, between the shock absorber and the tooth attachment portion, for engagement with a tightening tool to facilitate rotation and installation of the base of the dental implant into bone of a patient.

18. The dental implant of claim 1, wherein the index collar, the central shaft, the plurality of arcuate flex struts, and the base are all cast and formed as a fluid tight single unit and a silicon seal seals between the central shaft and a collar aperture of the index collar.

19. A dental implant comprising:
   a base having an exterior thread for engagement with bone of a patient;
   a central shaft supporting a plurality of shock absorbing arcuate flex struts adjacent a second end thereof and having an external threaded tooth attachment portion adjacent a first end thereof for engagement with a dental prostheses;
   the plurality of arcuate flex struts coupling the base to the second end of the central shaft such that a first end of each of the plurality of flex struts being directly attached to the central shaft while a second end of each of the plurality of flex struts being directly attached to the base to allow limited movement between the central shaft and the base, and each one of the arcuate flex struts initially projecting toward the second end of the central shaft before bending back toward the first end of the central shaft and then directly attaching to the base;
   an index collar extending between the central shaft and the base and the index collar having a collar aperture through which the central shaft passes; and
   a plurality of index tabs being provided along a circumference of the central shaft, between the shock absorber and the tooth attachment portion, for engagement with a tightening tool to facilitate rotation and installation of the base of the dental implant into the bone of the patient.

20. The dental implant of claim 19, wherein the index collar, the central shaft, the plurality of arcuate flex struts, and the base are all cast and formed as a fluid tight single unit and a silicon seal seals between the central shaft and a collar aperture of the index collar.

* * * * *